United States Patent
Okuda et al.

(10) Patent No.: US 9,936,888 B2
(45) Date of Patent: Apr. 10, 2018

(54) PULSE PERIOD CALCULATION DEVICE AND BIOSENSOR EQUIPPED WITH THE SAME

(71) Applicant: MURATA MANUFACTURING CO., LTD., Nagaokakyo-shi, Kyoto-Fu (JP)

(72) Inventors: Noriaki Okuda, Nagaokakyo (JP); Eiji Takahasi, Nagaokakyo (JP)

(73) Assignee: MURATA MANUFACTURING CO., LTD., Nagaokakyo-Shi, Kyoto-Fu (JP)

(*) Notice: Subject to any disclaimer, the term of this patent is extended or adjusted under 35 U.S.C. 154(b) by 739 days.

(21) Appl. No.: 13/860,241

(22) Filed: Apr. 10, 2013

(65) Prior Publication Data

US 2013/0267859 A1  Oct. 10, 2013

Related U.S. Application Data

(63) Continuation of application No. PCT/JP2011/067458, filed on Jul. 29, 2011.

(30) Foreign Application Priority Data

Oct. 14, 2010  (JP) .................................. 2010-231063
Jan. 6, 2011  (JP) .................................. 2011-000945

(51) Int. Cl.
*A61N 1/378* (2006.01)
*A61B 5/04* (2006.01)
(Continued)

(52) U.S. Cl.
CPC .......... *A61B 5/04012* (2013.01); *A61B 5/021* (2013.01); *A61B 5/02007* (2013.01);
(Continued)

(58) Field of Classification Search
CPC .................................................. A61B 5/0245
See application file for complete search history.

(56) References Cited

U.S. PATENT DOCUMENTS 4,463,425 A  7/1984  Hirano et al.
4,960,126 A  10/1990  Conlon et al.
(Continued)

FOREIGN PATENT DOCUMENTS

JP  57-022736 A  2/1982
JP  2003-339651 A  12/2003
(Continued)

OTHER PUBLICATIONS

PCT/JP2011/067458 Written Opinion dated Oct. 26, 2011.

*Primary Examiner* — Carl H Layno
*Assistant Examiner* — Jennifer Ghand
(74) *Attorney, Agent, or Firm* — Arent Fox LLP

(57) ABSTRACT

A device for calculating a pulse period of a living body. The device includes a maximum value detecting unit that detects a maximum value of a biological signal received at a predetermined time interval, a peak value determining unit that determines whether the maximum value is a peak value of the biological signal detected by the maximum value detecting unit during a fixed time period, a calculating unit that calculates a rhythmic pulse period of a living body generating the biological signal based on a time interval between successive peak values of the biological signal; and a fixed time period changing unit that changes the fixed time period to a predetermined time period that corresponds to the time interval between the successive peak values of the biological signal.

19 Claims, 7 Drawing Sheets

(51) Int. Cl.
 *A61B 5/0245* (2006.01)
 *A61B 5/0456* (2006.01)
 *A61B 5/02* (2006.01)
 *A61B 5/021* (2006.01)
 *A61B 5/0452* (2006.01)
 *A61B 5/00* (2006.01)
 *A61B 5/024* (2006.01)

(52) U.S. Cl.
 CPC ........ *A61B 5/0245* (2013.01); *A61B 5/02416* (2013.01); *A61B 5/0452* (2013.01); *A61B 5/0456* (2013.01); *A61B 5/7203* (2013.01); *A61B 5/02125* (2013.01); *A61B 5/7239* (2013.01)

(56) References Cited

U.S. PATENT DOCUMENTS

| | | | |
|---|---|---|---|
| 6,438,196 B1 | 8/2002 | Cesmeli | |
| 2006/0224074 A1* | 10/2006 | Ouchi | A61B 5/04525 600/513 |
| 2009/0204011 A1* | 8/2009 | Suzuki | A61B 5/02416 600/500 |

FOREIGN PATENT DOCUMENTS

| | | |
|---|---|---|
| JP | 2008-220556 A | 9/2008 |
| JP | 2009-112624 A | 5/2009 |
| JP | 2010-051387 A | 3/2010 |
| WO | WO-2005/027720 A2 | 3/2005 |
| WO | WO-2010-113354 A1 | 10/2010 |
| WO | WO-2010-125705 A1 | 11/2010 |

\* cited by examiner

PULSE PERIOD CALCULATION DEVICE AND BIOSENSOR EQUIPPED WITH THE SAME

CROSS REFERENCE TO RELATED APPLICATIONS

The present application is a continuation of International Application No. PCT/JP2011/067458, filed Jul. 29, 2011, which claims priority to Japanese Patent Application No. 2010-231063, filed Oct. 14, 2010, and Japanese Patent Application No. 2011-000945, filed Jan. 6, 2011, the entire contents of each of which are incorporated herein by reference.

FIELD OF THE INVENTION

The present invention relates to pulse period calculation devices that calculate the rhythmic period of a pulse of a living body from a biological signal, and relates to biosensors equipped with pulse period calculation devices.

BACKGROUND OF THE INVENTION

In the related art, an example of such a pulse period calculation device is a heartbeat measurement device disclosed in Patent Document 1.

In this heartbeat measurement device, a peak holding signal having a stepped waveform is generated as a result of a heartbeat waveform signal being subjected to peak holding by a peak holding unit. A pattern detection and period determining unit detects a pattern in which there are successive increases in signal level from the generated peak holding signal and matches this pattern to a P wave and an R wave in an electrocardiogram. Then, when the time interval between a peak that corresponds to the P wave and a peak that corresponds to the R wave is within a predetermined range and the difference in level value between the peaks exceeds a threshold, these peaks are regarded with certainty as being peaks that correspond to the P wave and the R wave and the larger peak is specified as being the R wave. When a pattern in which there are successive increases in signal level is not detected, a pattern of successive decreases in signal level is complimentarily detected and this pattern is matched to an R wave and a T wave in an electrocardiogram. Then, regarding the peak corresponding to the R wave and the peak corresponding to the T wave, the larger of these peaks is specified as the R wave by performing similar processing to as in the case of the P wave and the R wave. The heart rate is then calculated from the time interval between R waves specified in this way.

In addition, in the related art, there is also a heartbeat measurement system disclosed in Patent Document 2, as an example of such a pulse period calculation device.

In this heartbeat measurement system, a heartbeat signal is detected from a measurement target by a signal detection device. The detected heartbeat signal is subjected to time division by a signal processing device and the obtained successive signals are compared to each other by the signal processing device. A peak value of the heartbeat signal is detected from the result of this comparison. In addition, the signal processing device generates a peak value group containing one or a plurality of peak values in heartbeat units of the heartbeat signal and standardizes each peak value of the peak value group by dividing each peak value of the peak value group by the largest peak value of the peak value group. Accordingly, by subjecting the standardized signal to addition and multiplication, the fine structure of the signal, which was liable to be overlooked conventionally, is revealed.

In addition, in the related art, there is also a pulse wave analysis device disclosed in Patent Document 3, as an example of such a pulse period calculation device.

In this pulse wave analysis device, a pulse wave is obtained on the basis of a pulse wave signal from a pulse wave sensor and the top point (peak) of the pulse wave corresponding to the contraction period of the heart is obtained as a result of a data processing device including the pulse wave analysis device searching for the top point of the obtained pulse wave. It is determined whether time intervals adjacent to the obtained top point are less than a predetermined time period expressed by a top point search correction coefficient t3. In this determination, if it is determined that the time intervals adjacent to the top point are equal to or more than the predetermined time period, the detected top point is counted as a true top point, which is not noise or the like, and the average number of times this top point occurs in one minute is calculated as the pulse rate. In addition, by extracting, or subtracting the base line of the pulse wave, a modified pulse wave that is close to a sin wave is obtained. When this modified pulse wave is subjected to complex demodulation analysis at the frequency of the pulse wave, the instantaneous frequency expressing a frequency f between peaks of the pulse waves is obtained and the pulse interval, which is the period T, is obtained from the frequency f. The top point search correction coefficient t3 is updated from the average value of the pulse interval and top point searching is accurately performed by removing noise.

CITATION LIST

Patent Document 1: Japanese Unexamined Patent Application Publication No. 2009-112624

Patent Document 2: Japanese Unexamined Patent Application Publication No. 2008-220556

Patent Document 3: Japanese Unexamined Patent Application Publication No. 2003-339651

However, the above-described heartbeat measurement device of the related art disclosed in Patent Document 1 determines the correspondence between the P wave and the R wave or between the R wave and the T wave and therefore it is necessary that the difference in level value between peaks exceed a certain threshold and that a lower peak value of the P wave and the T wave has a signal level that is not obscured by noise. Consequently, in the heartbeat measurement device of the related art disclosed in Patent Document 1, in the case where the level of a heartbeat waveform signal of a living body obtained from the sensor is low, a peak cannot be determined.

In addition, in the heartbeat measurement system of the related art disclosed in Patent Document 2, for example, division processing for standardizing the peak values of a group of peak values of a heartbeat signal, indexing processing in which the intensities of peak addresses are indexed by using a logarithmic function, and processing in which waveform signals, in which information on the group of peak addresses is formed, are added together and averaged, are necessary. Consequently, the heartbeat measurement system of the related art disclosed in Patent Document 2 employs complex arithmetical processing that is lacking in convenience and reductions in the size and cost of the device cannot be achieved.

In addition, in the pulse wave analysis device of the related art disclosed in Patent Document 3, a pulse time interval used for updating the top point search correction coefficient t3 is obtained by carrying out complicated complex demodulation analysis in which, for example, a complex trigonometrical function having a frequency in the center of a frequency range that is desired to be analyzed is applied to the pulse wave signal, or the pulse wave signal is multiplied by a complex trigonometrical function having a frequency in the center of a frequency range that is desired to be analyzed and the real and imaginary parts of the components in the frequency range that is desired to be analyzed are converted into a polar coordinate system. Consequently, the pulse wave analysis device of the related art disclosed in Patent Document 3 employs complex arithmetical processing that is lacking in convenience and reductions in the size and cost of the device cannot be achieved.

SUMMARY OF THE INVENTION

The present invention was made in order to solve the above-described problems and provides a pulse period calculation device that includes maximum value detecting means that detects a maximum value of a biological signal obtained at a predetermined time interval, peak value determining means that, in a case where a maximum value that is larger than the maximum value detected by the maximum value detecting means is not detected within a fixed time period by the maximum value detecting means, determines that the maximum value detected by the maximum value detecting means is a peak value, calculating means that, on the basis of a time interval between successive peak values determined by the peak value determining means, calculates a rhythmic period of a pulse of a living body that generates the biological signal, and fixed time period changing means that, in accordance with the time interval between successive peak values determined by the peak value determining means, successively changes the fixed time period to a corresponding one of a plurality of time periods predetermined in accordance with the time interval between the peak values.

With this configuration, the maximum value of a biological signal obtained at a predetermined time interval is detected by the maximum value detecting means, and in the case where a maximum value that is larger than the detected maximum value is not detected by the maximum value detecting means within a fixed time period, the maximum value detected by the maximum value detecting means is determined to be a peak value by the peak value determining means. The rhythmic period of a pulse of a living body is calculated by the calculating means on the basis of the time interval between successive peak values determined by the peak value determining means.

Accordingly, in contrast to the device of the related art disclosed in Patent Document 1, even in a case where the level of a biological signal obtained from a sensor is low, so long as the maximum value of the biological signal detected by the maximum value detecting means is a signal level that is not obscured by noise, a peak value can be determined and the rhythmic period of the pulse can be calculated. In addition, even if a base line, which serves as a reference for the amplitude of the biological signal, varies, similarly, so long as the maximum value of the biological signal detected by the maximum value detecting means is a signal level that is not obscured by noise, a peak value can be determined and the rhythmic period of the pulse can be calculated.

In addition, in accordance with the time interval between successive peak values determined by the peak value determining means, the fixed time period used in the determination of the peak value is successively changed by the fixed time period changing means to a corresponding one of a plurality of time periods predetermined in accordance with the time interval between the peak values. Accordingly, in contrast to in the devices of the related art disclosed in Patent Document 2 and Patent Document 3 in which the determination of the peak value is performed using complex arithmetical processing such as division, the determination of the peak value is performed using simple arithmetic processing, that is, processing in which the magnitude of an obtained biological signal is subjected to a simple comparison, processing in which a fixed time period and a time interval between peak values are counted, and processing in which a corresponding one of a plurality of predetermined time periods is selected in accordance with a time interval between peak values. As a result, the rhythmic period of a pulse of a living body that continuously varies can be appropriately calculated at all times by simple arithmetical processing and size and cost reduction of the pulse period calculation device can be achieved.

The present invention is characterized in that, when a maximum value that is larger than a maximum value detected by the maximum value detecting means is detected within a fixed time period by the maximum value detecting means, in the case where a maximum value that is even larger than the larger maximum value is not detected by the maximum value detecting means within a fixed time period from a time point at which the larger maximum value was detected, the peak value determining means determines that the larger maximum value detected by the maximum value detecting means is a peak value.

According to this configuration, when a maximum value that is larger than a maximum value detected by the maximum value detecting means is detected within the fixed time period by the maximum value detecting means, counting of the fixed time period is restarted from the time point at which the larger maximum value was detected. Then, in the case where a maximum value that is even larger than the larger maximum value is not detected by the maximum value detecting means within this fixed time period, the larger maximum value detected by the maximum value detecting means is determined to be the peak value by the peak value determining means.

Accordingly, regarding a maximum value detected once by the maximum value detecting means, if a maximum value that is larger than that maximum value is detected by the maximum value detecting means within the fixed time period, the first maximum value is not used in the peak determination and is excluded from the calculation data for the rhythmic period of the pulse. As a result, among maximum values detected by the maximum value detecting means, for example, maximum values that correspond to signals of the P wave and T wave of a heartbeat signal and maximum values caused by noise, that are not appropriate for use in calculation of the rhythmic period of the pulse, are not used as targets of peak determination, and only maximum values which are appropriate for use in calculation of the rhythmic period of the pulse corresponding to an R wave signal are used as the targets of peak determination, whereby the accuracy with which the rhythmic period of the pulse is calculated is improved.

The present invention is characterized in that the fixed time period changing means successively changes the fixed time period in accordance with the time interval between successive peak values, which are determined by the peak value determining means and lie within a predetermined range.

According to this configuration, the fixed time period used in determination of the peak value is successively changed by the fixed time period changing means in accordance with the time interval between successive peak values, which are determined by the peak value determining means and lie within a predetermined range.

Accordingly, in the case where successive peak values determined by the peak value determining means do not lie within the predetermined range, it is assumed that the peak values are not peak value of the same type and the fixed time period used in the determination of the peak value is not changed in accordance with the time interval between those peak values. On the other hand, in the case where the successive peak values lie within the predetermined range, it is assumed that they are peak values of the same type and the fixed time period used in the determination of the peak values is changed in accordance with the time interval between these peak values. Therefore, the fixed time period used in the determination of the peak values is changed in accordance with the time interval between peak values that closely resemble each other and is changed so as to accurately follow transitions in the rhythmic period of the pulse, rather than being changed on the basis of for example peak values caused by noise. As a result, the rhythmic period of a pulse of a living body that continuously varies is appropriately calculated at all times by simple arithmetic processing.

The present invention is characterized in that the biological signal is a heartbeat signal and the calculating means calculates the rhythmic period of a pulse as a heart rate.

According to this configuration, the rhythmic period of a pulse is calculated as a heart rate by the calculating means on the basis of the time interval between successive peak values of a heartbeat signal determined by the peak value determining means.

The present invention is characterized in that the biological signal is a pulse wave signal and the calculating means calculates the rhythmic period of a pulse as a pulse rate.

According to this configuration, the rhythmic period of the pulse is calculated as a pulse rate by the calculating means on the basis of the time interval between successive peak values of a pulse wave signal determined by the peak value determining means.

The present invention is characterized in that the maximum value detecting means is formed of heartbeat maximum value detecting means that detects a maximum value of a heartbeat signal obtained at a predetermined time interval and pulse wave maximum value detecting means that detects a maximum value of an acceleration pulse wave signal obtained by subjecting a pulse wave signal obtained at a predetermined time interval to differentiation two times, the peak value determining means is formed of heartbeat peak value determining means that, in a case where a maximum value that is larger than the maximum value of the heartbeat signal detected by the heartbeat maximum value detecting means is not detected by the heartbeat maximum value detecting means within a fixed time period for heartbeat peak value determination, determines that the maximum value of the heartbeat signal detected by the heartbeat maximum value detecting means is a heartbeat peak value, and pulse wave peak value determining means that, in a case where a maximum value that is larger than the maximum value of the acceleration pulse wave signal detected by the pulse wave maximum value detecting means is not detected by the pulse wave maximum value detecting means within a fixed time period for acceleration pulse wave peak value determination, determines that the maximum value of the acceleration pulse wave signal detected by the pulse wave maximum value detecting means is an acceleration pulse wave peak value, the calculating means calculates a pulse wave propagation time period from a time difference between the heartbeat peak value determined by the heartbeat peak value determining means and the acceleration pulse wave peak value determined by the pulse wave peak value determining means, and the fixed time period changing means is formed of fixed time period changing means, which is for heartbeat peak value determination, that, in accordance with a time interval between successive heartbeat peak values determined by the heartbeat peak value determining means, successively changes a fixed time period for heartbeat peak value determination to a corresponding one of a plurality of time periods predetermined in accordance with the time interval between heartbeat peak values, and fixed time period changing means, which is for pulse wave peak value determination, that, in accordance with a time interval between successive acceleration pulse wave peak values determined by the pulse wave peak value determining means, successively changes a fixed time period for acceleration pulse wave peak value determination to a corresponding one of a plurality of time periods predetermined in accordance with the time interval between the acceleration pulse wave peak values.

According to this configuration, in the case where a maximum value that is larger than the maximum value of the heartbeat signal detected by the heartbeat maximum value detecting means is not detected by the heartbeat maximum value detecting means within the fixed time period for heartbeat peak value determination, the maximum value of the heartbeat signal detected by the heartbeat maximum value detecting means is determined to be the heartbeat peak value by the heartbeat peak value determining means. In addition, in the case where a maximum value that is larger than the maximum value of the acceleration pulse wave signal detected by the pulse wave maximum value detecting means is not detected by the pulse wave maximum value detecting means within the fixed time period for acceleration pulse wave peak value determination, the maximum value of the acceleration pulse wave signal detected by the pulse wave maximum value detecting means is determined to be the acceleration pulse wave peak value by the pulse wave peak value determining means. Then, the time difference between the heartbeat peak value determined by the heartbeat peak value determining means and the acceleration pulse wave peak value determined by the pulse wave peak value determining means is calculated as the pulse wave propagation time period by the calculating means. Accordingly, the time taken for a pulse wave to propagate in an artery due to pulse is known from the calculated pulse wave propagation time period and therefore the age of a blood vessel can be estimated and the blood pressure can be calculated.

The present invention is characterized in that the pulse period calculation device further includes amplifying means that amplifies the biological signal at an amplification ratio, or factor in accordance with a control signal and outputs the amplified signal to the maximum value detecting means, and reference value detecting means that detects as a reference value, a magnitude, at a predetermined timing, of the biological signal amplified by the amplifying means, where the calculating means calculates a magnitude of the peak value determined by the peak value determining means from a difference between the peak value determined by the peak value determining means and the reference value detected by the reference value detecting means, and outputs a control signal based on the magnitude of the calculated peak value to the amplifying means.

According to this configuration, the magnitude of a peak value is calculated by the calculating means from the difference between the peak value determined by the peak value determining means and the reference value detected by the reference value detecting means, and a control signal based on the calculated magnitude of the peak value is output to the amplifying means and the amplification ratio of the amplifying means is changed. Therefore, the amplifying means, which performs amplification at an amplification ratio in accordance with the control signal, amplifies the biological signal at an amplification ratio based on the magnitude of the calculated peak value.

Accordingly, in a case where the calculated magnitude of the peak value is large, the calculating means changes the control signal to a control signal that makes the amplification ratio of the amplifying means small, and in a case where the calculated magnitude of the peak value is small, the calculating means changes the control signal to a control signal that makes the amplification ratio of the amplifying means large, whereby the magnitude of the biological signal obtained through amplification performed by the amplifying means is appropriately controlled to a magnitude that is appropriate for maximum value detection of a biological signal by the maximum value detecting means and peak value determination by the peak value determining means. As a result, erroneous detection of the maximum value of a biological signal by the maximum value detecting means and erroneous determination of a peak value by the peak value determining means is eliminated, whereby the accuracy with which a peak value is detected is improved.

The present invention is characterized in that the predetermined timing of the biological signal is a timing at which an ST segment of the biological signal, which is composed of a P wave, a Q wave, an R wave, an S wave, a T wave and a U wave, appears.

According to this configuration, the reference value detected by the reference value detecting means is a value of the ST segment of the biological signal, that is, a base line value that serves as a reference for the amplitude of the biological signal. Accordingly, the magnitude of the peak value calculated by the calculating means is a magnitude that is relative to the base line and therefore is easy to evaluate.

The present invention is characterized in that the calculating means calculates the magnitudes of peak values from differences between a plurality of peak values successively determined by the peak value determining means and a plurality of reference values that correspond to the peak values and are successively detected by the reference value detecting means, and in the case where the calculated magnitudes of the peak values are successively within a predetermined range, the calculating means changes the control signal output to the amplifying means.

With this configuration, in the case where the difference between a peak value and a reference value calculated a plurality of times by the calculating means is successively within a predetermined range, the control signal output to the amplifying means is changed, whereby the amplification ratio of the amplifying means is changed. Consequently, in the case where the magnitudes of peak values are successively and stably within a predetermined range, the amplification ratio of the amplifying means is changed and therefore erroneous changing of the amplification ratio of the amplifying means due to erroneous determination of the magnitude of a peak value is avoided.

The present invention provides a bio-sensor that includes any of the above-described pulse period calculation devices.

According to the present invention, a bio-sensor is provided that exhibits each of the above-described effects.

According to the present invention, as has been described above, provided that the maximum value of a biological signal detected by the maximum value detecting means is a signal level that is not obscured by noise, it is possible to determine a peak value and calculate the rhythmic period of a pulse. In addition, the rhythmic period of the pulse of a living body that is continuously varying can be appropriately calculated at all times by simple arithmetic processing and size and cost reduction of the pulse period calculation device can be achieved.

DETAILED DESCRIPTION OF THE PREFERRED EMBODIMENTS OF THE INVENTION

Next, a first embodiment will be described in which a pulse period calculation device according to the present invention is used to calculate a heart rate.

Figure 1:
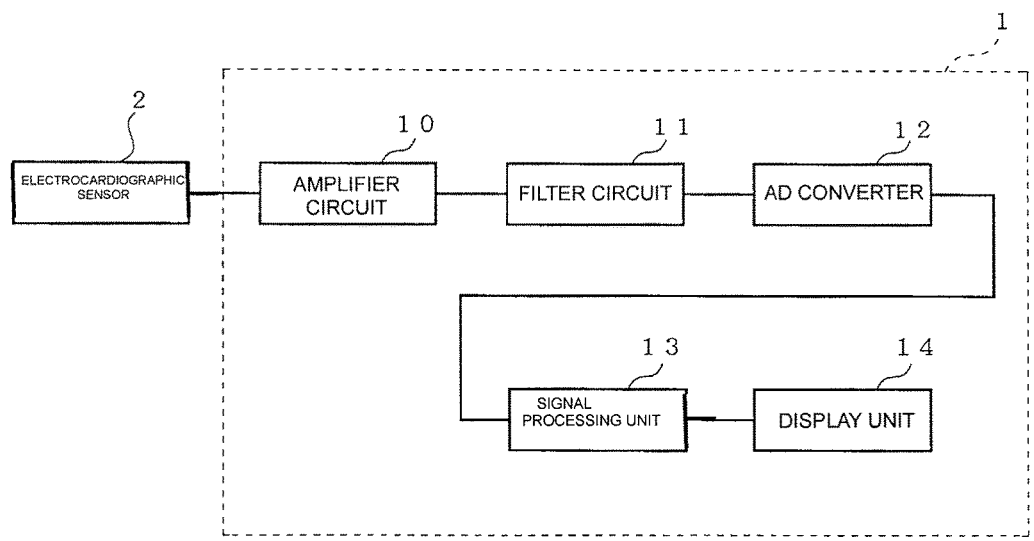
FIG. 1 is a block diagram illustrating the electrical circuit configuration of a pulse period calculation device according to a first embodiment of the present invention.

FIG. 1 is a block diagram illustrating the electrical circuit configuration of a pulse period calculation device according to this embodiment.

An electrocardiographic sensor 2 is connected to a pulse period calculation device 1. The electrocardiographic sensor 2 is in contact with a living body such as a human or an animal at a predetermined position and detects the change with time of the action potential of the heart, which changes with the beating of the heart of the living body and outputs this change as a heartbeat signal, which is a biological signal, to the pulse period calculation device 1.

Figure 2:
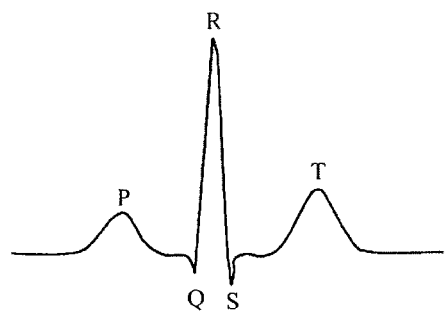
FIG. 2 illustrates a representative normal waveform of a heartbeat signal.

A representative normal waveform corresponding to one cycle of a heartbeat of a heartbeat signal is illustrated in FIG. 2. This heartbeat signal waveform is formed of five waves, which are a P wave, a Q wave, an R wave, an S wave and a T wave, as well as a U wave which is not illustrated. The Q wave, the R wave and the S wave are collectively called a QRS wave. The P wave is the wave of an action potential arising from excitation of an atrium of the heart, the QRS wave is the wave of an action potential arising from excitation of a ventricle of the heart, and the T wave is the wave of an action potential arising in a process in which myocardial cells of an excited ventricle are repolarized.

The pulse period calculation device 1 includes an amplifier circuit 10, a filter circuit 11, an AD converter 12, a signal processing unit 13 and a display unit 14. A heartbeat signal output from the electrocardiographic sensor 2 to the pulse period calculation device 1 is amplified by the amplifier circuit 10 and has noise components removed therefrom by the filter circuit 11. The heartbeat signal from which noise components have been removed is converted from an analog signal to a digital signal by the AD converter 12 and the converted signal is supplied to the signal processing unit 13. The signal processing unit 13 is formed of a microcomputer including a central processing unit (CPU), a read-only memory (ROM) and a readable/writable memory (RAM). The CPU calculates a heart rate by performing predetermined arithmetical processing in accordance with a heart rate calculation program stored in the ROM while using the RAM as a temporary storage work area. The calculated heart rate is displayed on the display unit 14, which is formed of a liquid crystal display (LCD), an organic electroluminescence (EL) device or the like.

The CPU of the signal processing unit 13 functions as maximum value detecting means, peak value determining means, calculating means and fixed time period changing means by utilizing the heart rate calculation program stored in the ROM.

Figure 3:
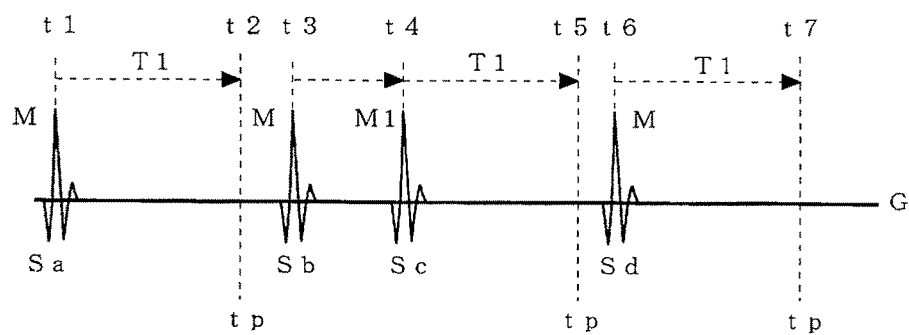
FIG. 3 illustrates a series of heartbeat signals for explaining peak value determination performed by a signal processing unit of the pulse period calculation device according to the first embodiment.

The maximum value detecting means obtains a heartbeat signal output from the electrocardiographic sensor 2 at a predetermined time interval and detects a maximum value M of the heartbeat signal. In this embodiment, the heartbeat signal is obtained at a sampling time interval of 600 [Hz] and the detected maximum value M of the heartbeat signal is stored in the RAM by the CPU. In the case where a maximum value M1 that is larger than a maximum value M detected by the maximum value detecting means is not detected within a fixed time period T1 by the maximum value detecting means, the peak value determining means determines that the maximum value M detected by the maximum value detecting means is a peak value P. For example, a series of heartbeat signals illustrated in FIG. 3 is obtained by the signal processing unit 13 and in the case where a maximum value M1 that is larger than a maximum value M, which was detected at a time t1 by the maximum value detecting means and corresponds to the R wave of a heartbeat signal Sa, is not detected within the fixed time period T1 by the maximum value detecting means, the peak value determining means determines that the maximum value M detected by the maximum value detecting means at the time t1 is a peak value P. A time t2, which is the fixed time period T1 after the time t1 and at which the peak value P is determined by the peak value determining means, is a peak determination point tp. The peak value P determined by the peak value determining means is stored in the RAM. Here, each heartbeat signal in the series of heartbeat signals oscillates about a base line G. In addition, the fixed time period T1 is a time period during which the maximum value M detected by the maximum value detecting means is not updated and is timed by counting performed in a maximum value update counter formed in a predetermined area of the RAM.

In this embodiment, when a maximum value M1 that is larger than the maximum value M detected by the maximum value detecting means is detected within the fixed time period T1 by the maximum value detecting means, in the case where a maximum value M2 that is even larger than the larger maximum value M1 is not detected by the maximum value detecting means within the fixed time period T1 from the time point at which the larger maximum value M1 was detected, the peak value determining means determines that the larger maximum value M1 detected by the maximum value detecting means is a peak value P. For example, as illustrated in FIG. 3, when a maximum value M1 of a heartbeat signal Sc that is larger than a maximum value M of a heartbeat signal Sb detected at a time t3 by the maximum value detecting means is detected at a time t4 within the fixed time period T1 from the time t3 by the maximum value detecting means, in the case where a maximum value M2 that is even larger than the larger maximum value M1 is not detected by the maximum value detecting means within the fixed time period T1 from the time t4 which is a time point at which the larger maximum value M1 was detected, the larger maximum value M1 detected by the maximum value detecting means is determined to be a peak value P at a peak determination point tp, which is a time t5 the fixed time period T1 after the time t4. Then, the determined peak value P is stored in the RAM.

After that, similarly, in the case where a maximum value M1 that is larger than a maximum value M of a heartbeat signal Sd detected at a time t6 by the maximum value detecting means is not detected within the fixed time period T1 by the maximum value detecting means, the peak value determining means determines that the maximum value M detected at the time t6 by the maximum value detecting means is a peak value P at a peak determination point tp which is a time t7 the fixed time period T1 after the time t6 and stores the peak value P in the RAM.

Figure 4:
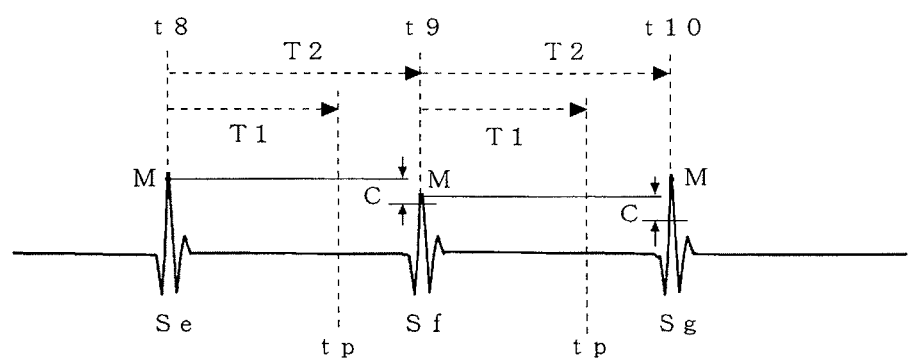
FIG. 4 illustrates a series of heartbeat signals for explaining a time interval between successive peak values calculated by the signal processing unit of the pulse period calculation device according to the first embodiment.

The calculating means obtains the number of peak values P that appear per minute on the basis of a time interval T2 between successive peak values P determined by the peak value determining means and calculates the rhythmic period of the pulse of the living body generating the biological signal as a heart rate. The time interval T2 between successive peak values P, for example, as illustrated in the series of heartbeat signals of FIG. 4, is the time interval between a time t8 at which a maximum value M of a heartbeat signal Se, which was determined to be a peak value P and stored in the RAM, was detected and a time t9 at which a maximum value M of a heartbeat signal Sf, which was determined to be a peak value P and stored in the RAM, was detected. Similarly, the time interval T2 is the time interval between the time t9 at which the maximum value M of the heartbeat signal Sf, which was determined to be a peak value P and stored in the RAM, was detected and a time t10 at which a maximum value M of a heartbeat signal Sg, which was determined to be a peak value P and stored in the RAM, was detected. Parts of FIG. 4 that are the same as FIG. 3 are denoted by the same reference symbols and description thereof is omitted. The time interval T2 between successive peak values P is timed by performing counting in a peak interval counter formed in a predetermined area of the RAM separate from the maximum value update counter that times the fixed time period T1 which is a period during which the maximum value M is not updated.

In the case where an initial maximum value M is determined to be a peak value P at a peak determination point tp immediately after the fixed time period T1 has elapsed and a maximum value M that appears immediately after that peak determination point tp is determined to be a peak value P at a subsequent peak determination point tp immediately after the subsequent fixed time period T1 has elapsed, the time interval T2 between peak values P is at its shortest and is slightly larger than the fixed time period T1. In addition, in a case where an initial maximum value M is determined to be the peak value P at a peak determination point tp immediately after the fixed time period T1 has elapsed and a maximum value M that appears immediately before the fixed time period T1 after that peak determination point tp has elapsed is determined to be the peak value P at a subsequent determination point tp immediately after the fixed time period T1 has elapsed after the peak determination point tp, the time interval T2 between peak values P is at its longest and is slightly smaller than two times the fixed time period T1. From the fact that the normal value of the heart rate of an adult is between 60 to 90 beats per minute, if the fixed time period T1 is set to 0.5 [seconds (s)], a time interval T2 between peak values P that slightly exceeds 0.5 [s] as a shortest value and is slightly lower than 1 [s], which is two times 0.5 [s], as a longest value is measured and a heart rate that exceeds 60 (=60÷1) and is less than 120 (=60÷0.5) is measured. However, in this case, only the normal heart rate of an adult can be measured. Consequently, in accordance with the time interval T2 between successive peak values P determined by the peak value determining means, fixed time period changing means successively changes the fixed time period T1 to a corresponding one of a plurality of time periods predetermined in accordance with the time interval T2 between the peak values P.

In this embodiment, when the time interval T2 between successive peak values P is more than 0.3 [s] and less than 0.5 [s], the fixed time period T1 is correspondingly predetermined to be 0.3 [s], when the time interval T2 between successive peak values P is more than 0.5 [s] and less than 0.6 [s], the fixed time period T1 is correspondingly predetermined to be 0.4 [s], when the time interval T2 between successive peak values P is more than 0.6 [s] and less than 0.8 [s], the fixed time period T1 is correspondingly predetermined to be 0.5 [s], and when the time interval T2 between successive peak values P is more than 0.8 [s], the fixed time period T1 is correspondingly predetermined to be 0.75 [s]. Thus, the fixed time period T1 is caused to change whenever necessary to an optimum time period from among the four time periods of 0.3 [s], 0.4 [s], 0.5 [s] and 0.75 [s].

The heart rate is measured in a range of more than 100 (=60÷0.6) and less than 200 (60÷0.3) when the fixed time period T1 is 0.3 [s], is measured in a range of more than 75 (=60÷0.8) and less than 150 (=60÷0.4) when the fixed time period T1 is 0.4 [s], is measured in a range of more than 60 (=60÷1.0) and less than 120 (=60÷0.5) when the fixed time period T1 is 0.5 [s] and is measured in a range of more than 40 (=60÷1.5) and less than 80 (=60÷0.75) when the fixed time period T1 is 0.75 [s]. As a result, the heart rate is measured in a range from 40 to 200 and therefore the heart rate of a person or an animal can be measured over a wide range without being limited to the normal heartbeat of an adult.

In addition, in this embodiment, the fixed time period changing means successively changes the fixed time period T1 in accordance with the time interval T2 between successive peak values P, which are determined by the peak value determining means and lie within a predetermined range. For example, as illustrated in FIG. 4, in the case where the peak value P of the heartbeat signal Sf has a maximum value M that is equal to or more than a value obtained by subtracting a fixed value C from a maximum value M taken as a peak value P of the heartbeat signal Se, a determination is made by the fixed time period changing means that the successive peak values P of the heartbeat signal Se and the heartbeat signal Sf are within a predetermined range. Similarly, in the case where the peak value P of the heartbeat signal Sg has a maximum value M that is equal to or more than a value obtained by subtracting the fixed value C from a maximum value M taken as the peak value P of the heartbeat signal Sf, a determination is made by the fixed time period changing means that the successive peak values P of the heartbeat signal Sf and the heartbeat signal Sg are within a predetermined range. In accordance with the time interval T2 between peak values P for which the determination has been made that the values of the peak values P are within a predetermined range, the fixed time period T1 is successively changed by the fixed time period changing means.

Next, heart rate calculation processing performed by the CPU in accordance with the heart rate calculation program in the signal processing unit 13 of the pulse period calculation device 1 according to this embodiment will be described while referring to the flowchart of FIG. 5.

Figure 5:
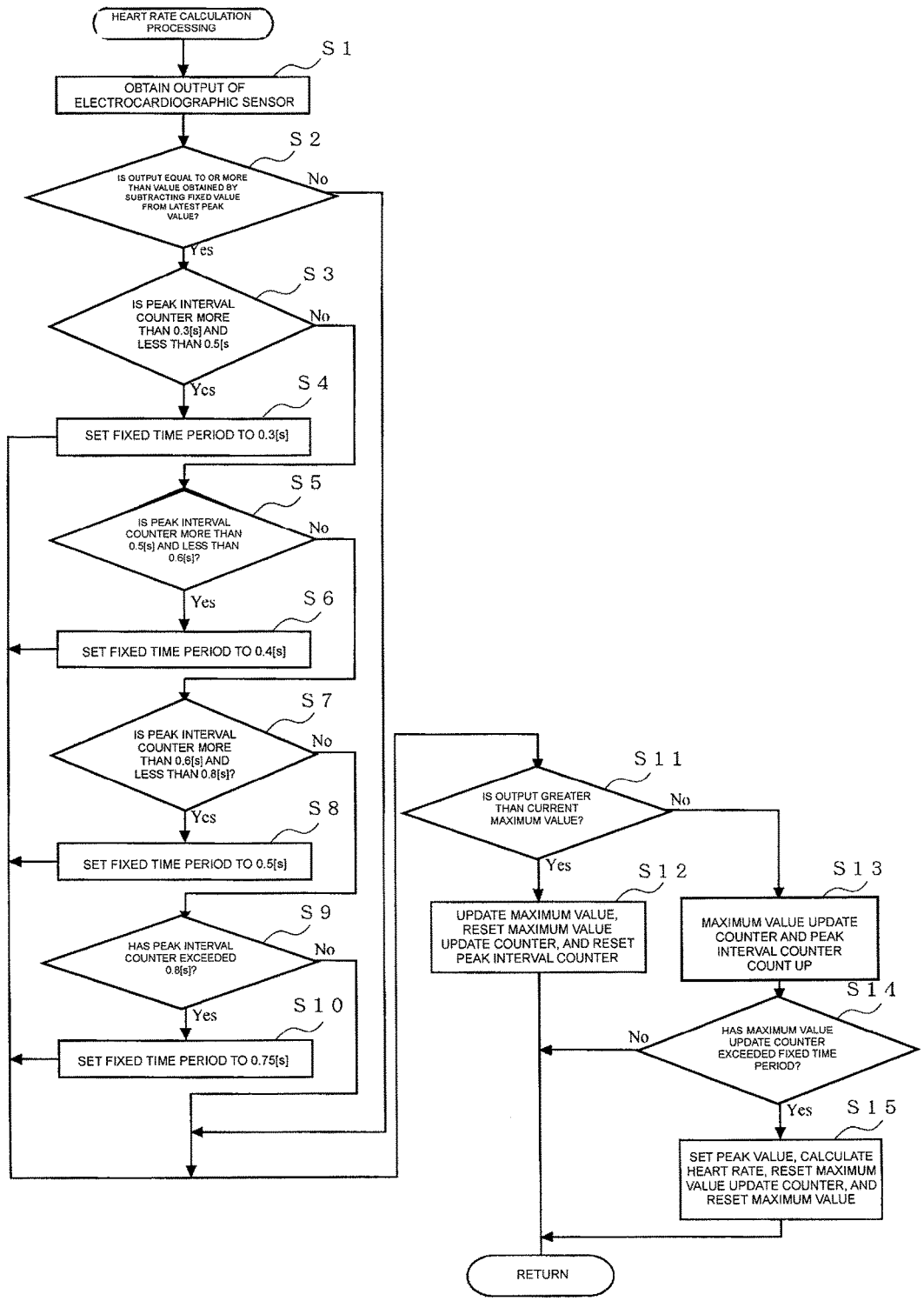
FIG. 5 is a flowchart illustrating heart rate calculation processing performed by the signal processing unit of the pulse period calculation device according to the first embodiment.

The CPU, first, in step (hereafter, "S") 1 of FIG. 5, obtains, at a predetermined time interval, a heartbeat signal that has been output from the electrocardiographic sensor 2, amplified by the amplifier circuit 10, had noise removed therefrom by the filter circuit 11 and converted into a digital signal by the AD converter 12. Next, in S2, the CPU determines whether or not a maximum value M of the heartbeat signal obtained at a predetermined time interval is equal to or more than a value obtained by subtracting a fixed value C from the latest peak value P stored in the RAM. In a case where the maximum value M of the obtained heartbeat signal is larger than or equal to a value obtained by subtracting the fixed value C from the latest peak value P and the determination result of S2 is Yes, the CPU, in S3, determines whether or not the time interval T2 between peak values P counted by the peak interval counter is more than 0.3 [s] and less than 0.5 [s]. In the case where the time interval T2 between peak values P is more than 0.3 [s] and less than 0.5 [s] and the determination result of S3 is Yes, the CPU sets the fixed time period T1 to 0.3 [s] in S4.

On the other hand, in the case where the time interval T2 between peak values P is not in a range of more than 0.3 [s] and less than 0.5 [s] and the determination result of S3 is No, the CPU, in S5, determines whether the time interval T2 between peak values P counted by the peak interval counter is more than 0.5 [s] and less than 0.6 [s]. In the case where the time interval T2 between peak values P is more than 0.5 [s] and less than 0.6 [s] and the determination result of S5 is Yes, the CPU sets the fixed time period T1 to 0.4 [s] in S6. On the other hand, in the case where the time interval T2 between peak values P is not in a range of more than 0.5 [s] and less than 0.6 [s] and the determination result of S5 is No, the CPU, in S7, determines whether the time interval T2 between peak values P counted by the peak interval counter is more than 0.6 [s] and less than 0.8 [s]. In the case where the time interval T2 between peak values P is more than 0.6 [s] and less than 0.8 [s] and the determination result of S7 is Yes, the CPU sets the fixed time period T1 to 0.5 [s] in S8. On the other hand, in the case where the time interval T2 between peak values P is not in a range of more than 0.6 [s] and less than 0.8 [s] and the determination result of S7 is No, the CPU, in S9, determines whether the time interval T2 between peak values P counted by the peak interval counter is more than 0.8 [s]. In the case where the time interval T2 between peak values P is more than 0.8 [s] and the determination result of S9 is Yes, the CPU sets the fixed time period T1 to 0.75 [s] in S10.

In the case where the time interval T2 between peak values P is not more than 0.8 [s] and the determination result of S9 is No, in the case where the maximum value M of the obtained heartbeat signal is not equal to more than a value obtained by subtracting the fixed value C from the latest peak value P and the determination result of S2 is No, or in the case where the fixed time period T1 has been set in S4, S6, S8 or S10, the CPU next determines in S11 whether or not the maximum value M of the heartbeat signal obtained in S1 is larger than the current maximum value M stored in the RAM. In the case where the maximum value M of the heartbeat signal obtained in S1 is larger than the current maximum value M of the heartbeat signal Sb stored in the RAM and the determination result of S11 is Yes, as is the case with the maximum value M1 of the heartbeat signal Sc illustrated in FIG. 3, the CPU, in S12, updates the current maximum value M stored in the RAM by overwriting it with the maximum value M of the heartbeat signal obtained in S1. Then, the maximum value update counter, which counts the fixed time period T1, and the peak interval counter, which counts the time interval T2 between peak values P, are reset and counting performed by the counters is restarted.

In addition, in the case where the maximum value M of the heartbeat signal obtained in S1 is not greater than the current maximum value M and the determination result of S11 is No, the CPU, in S13, counts up a count value of the maximum value update counter and a count value of the peak interval counter and timing progresses. Next, the CPU, in S14, determines whether a time period timed by the maximum value update counter has exceeded the fixed time period T1. In the case where the time period timed by the maximum value update counter is more than the fixed time period T1 and the determination result of S14 is Yes, the CPU, in S15, determines that the maximum value M of the heartbeat signal obtained in S1 is a peak value P and sets the maximum value M as the latest peak value P and stores it in the RAM. Then, the CPU obtains the number of peak values P per minute from the time interval T2 between this latest peak value P and the immediately previous peak value P and calculates the heart rate. Then, the maximum value update counter is reset and the maximum value M stored in the RAM and determined as the peak value P this time is reset.

In the case where the time period timed by the maximum value update counter is not greater than the fixed time period T1 and the determination result of S14 is No, or after the processing of S12 or S15 has finished, the CPU returns to the processing of S1 and repeats performance of the above-described processing operations.

With the pulse period calculation device 1 according to this embodiment, in the case where a maximum value M of the heartbeat signal obtained at a predetermined time interval is detected by the maximum value detecting means, and, in the processing of S11 and S14, a maximum value M that is larger than the detected maximum value M is not detected within the fixed time period T1 by the maximum value detecting means, in the processing of S15, the maximum value M detected by the maximum value detecting means is determined to be a peak value P by the peak value determining means. Then, the heart rate is calculated by the calculating means on the basis of the time interval T2 between successive peak values P determined by the peak value determining means.

Accordingly, the pulse period calculation device 1 according to this embodiment differs from the device of the related art disclosed in Patent Document 1 in that, even in the case in which the level of a heartbeat signal obtained from the electrocardiographic sensor 2 is low, so long as a maximum value M of the heartbeat signal detected by the maximum value detecting means is a signal level that is not obscured by noise, the peak value P can be determined and the heart rate can be calculated even when the P wave and the T wave of a heartbeat signal (refer to FIG. 2) are obscured by noise. In addition, even if a base line G (refer to FIG. 3), which serves as a reference for the amplitude of the heartbeat signal, varies, similarly, so long as the maximum value P of the heartbeat signal detected by the maximum value detecting means is a signal level that is not obscured by noise, the peak value P can be determined and the heart rate can be calculated.

In addition, in accordance with the time interval T2 between successive peak values P determined by the peak value determining means, the fixed time period T1 used in the determination of the peak value P is successively changed in the processing of S3 to S10 by the fixed time period changing means to a corresponding one of a plurality of time periods 0.3 [s], 0.4 [s], 0.5 [s] and 0.75 [s] predetermined in accordance with the time interval T2 between the peak values P. Accordingly, in contrast to in the devices of the related art disclosed in Patent Document 2 and Patent Document 3 in which the determination of the peak value P is performed using complex arithmetical processing such as division, the determination of the peak value P is performed using simple arithmetic processing, i.e., the processing of S11 in which the magnitude of an obtained heartbeat signal is subjected to a simple comparison, the processing of S13 in which the fixed time period T1 and the time interval T2 between peak values P are counted, and the processing of S3 to S10 in which a corresponding one of a plurality of predetermined time periods is selected in accordance with the time interval T2 between peak values P. As a result, a heart rate which is continuously varying can be appropriately calculated at all times by using simple arithmetic processing and size and cost reduction can be achieved for the pulse period calculation device 1.

In addition, with the pulse period calculation device 1 according to this embodiment, for example, in the processing of S11, if a maximum value M1 that is larger than the maximum value M of the heartbeat signal Sb detected by the maximum value detecting means is detected within the fixed time period T1 from the time t3 by the maximum value detecting means as in the case of the heartbeat signal Sc illustrated in FIG. 3, counting of the fixed time period T1 is restarted by the processing of S12 from the time t4, which is a time point at which the larger value M1 was detected. Then, in the subsequent processing of S11 and S14, in the case where a maximum value M2 that is even larger than the larger maximum value M1 is not detected by the maximum value detecting means within the fixed time period T1, in the processing of S15, the larger maximum value M1 detected by the maximum value detecting means is determined to be the peak value P by the peak value determining means.

Accordingly, regarding a maximum value M detected initially by the maximum value detecting means, if a maximum value M1 that is larger than that maximum value M is detected by the maximum value detecting means within the fixed time period T1, the maximum value M is not used in the peak determination and is excluded from the heart rate calculation data. As a result, among maximum values M detected by the maximum value detecting means, for example, maximum values M that correspond to signals of the P wave and T wave of a heartbeat signal and maximum values M caused by noise, that are not appropriate for use in calculation of the heart rate, are not used as targets of peak determination, and only maximum values M corresponding to the R wave which are appropriate for use in calculation of the heart rate are used as targets of peak determination, whereby the accuracy with which the heart rate is calculated is improved.

In addition, with the pulse period calculation device 1 according to this embodiment, the fixed time period T1 used in determination of the peak value P is successively changed by the fixed time period changing means in the processing of S3 to S10 in accordance with the time interval T2 between successive peak values P which lie within a predetermined range and include peak values P that are equal to or greater than a value obtained by subtracting a fixed value C from the previous peak value P, as is the case for the heartbeat signal Sf and the heartbeat signal Sg illustrated in FIG. 4.

Accordingly, in the case where successive peak values P determined by the peak value determining means do not lie within the predetermined range, it is assumed that the peak values P are not peak value P of the same type and the fixed time period T1 used in the determination of the peak values P is not changed in accordance with the time interval T2 between these peak values P. On the other hand, in the case where the successive peak values P lie within the predetermined range, it is assumed that they are peak values P of the same type and the fixed time period T1 used in the determination of the peak values P is changed in accordance with the time interval T2 between these peak values P. Therefore, the fixed time period T1 used in the determination of the peak values P is changed in accordance with the time interval T2 between peak values P that closely resemble each other and is changed so as to accurately follow transitions in the heart rate, rather than being changed on the basis of for example peak values P caused by noise. As a result, the heart rate of a living body that is continuously varying is appropriately calculated at all times by simple arithmetic processing.

In the above-described embodiment, description was given of a configuration in which a biological signal is a heartbeat signal detected by the electrocardiographic sensor 2 and the pulse period calculation device 1 calculated the rhythmic period of a pulse as a heart rate, but the present invention is not limited to this configuration. For example, a configuration may be adopted in which the biological signal is a pulse wave signal detected by a pulse wave sensor and the pulse period calculation device 1 calculates the rhythmic period of a pulse as a pulse rate.

Figure 6:
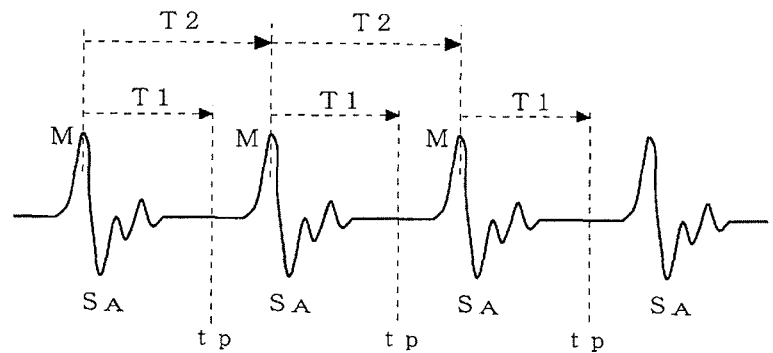
FIG. 6 illustrates a series of acceleration pulse wave signals calculated by the pulse period calculation device according to the first embodiment when calculating the pulse rate.

In this configuration, in the signal processing unit 13, a pulse wave signal obtained from a pulse wave sensor is subjected to differentiation two times to obtain an acceleration pulse wave signal and for example the rhythmic period of a pulse is calculated as a pulse rate on the basis of a time interval T2 between successive peak values P of acceleration pulse wave signals $S_A$ in series of acceleration pulse wave signals as illustrated in FIG. 6. Here, in the case where a maximum value M of an acceleration pulse wave signal $S_A$ is detected by the maximum value detecting means and a maximum value M that is larger than the detected maximum value M is not detected by the maximum value detecting means within a predetermined time period T1, the maximum value M detected by the maximum value detecting means is determined to be a peak value P at a peak determination point tp by the peak value determining means and stored in the RAM. Then, the pulse rate is calculated by the calculating means on the basis of the time interval T2 between successive peak values P determined by the peak value determining means. Here, instead of subjecting a pulse wave signal obtained from the pulse wave sensor to differentiation two times to obtain an acceleration pulse wave signal, a configuration may be adopted in which the pulse rate is calculated on the basis of the time interval T2 between successive peak values P of pulse wave signals.

Also with this configuration, provided that the maximum value M of an acceleration pulse wave signal $S_A$ or a pulse wave signal detected by the maximum value detecting means is a signal level that is not obscured by noise, the pulse period calculation device 1 can determine a peak value P and calculate a pulse rate and the same operational effects as in the above-described embodiment are attained.

Next, a second embodiment will be described in which a pulse period calculation device according to the present invention is used to calculate a pulse wave propagation time period.

Figure 7:
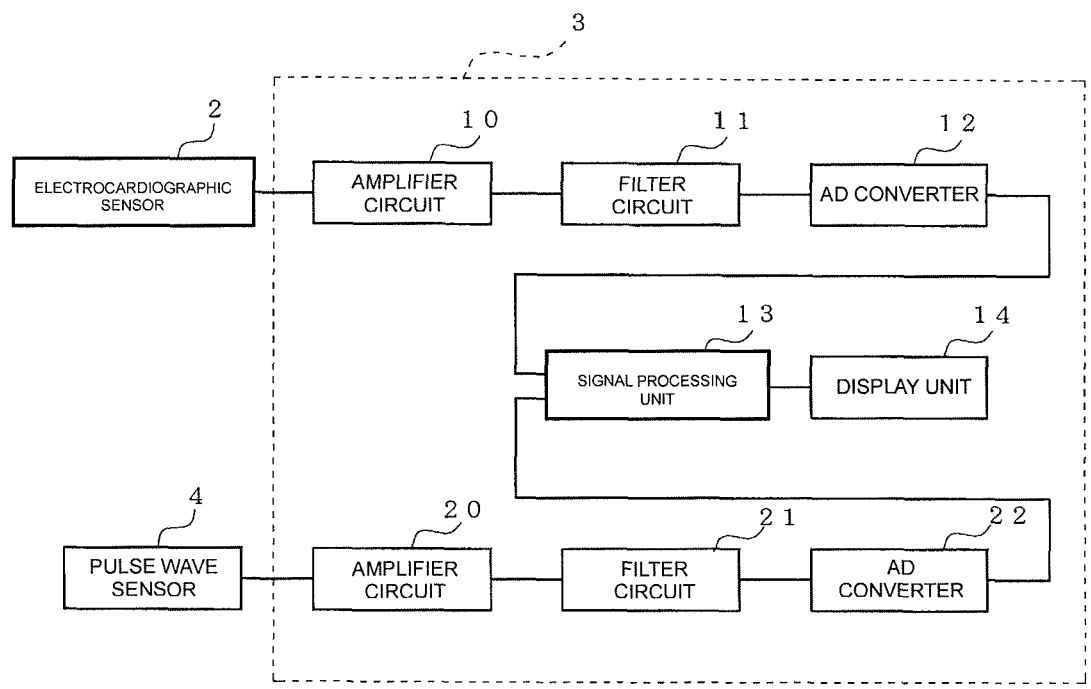
FIG. 7 is a block diagram illustrating the electrical circuit configuration of a pulse period calculation device according to a second embodiment of the present invention.

FIG. 7 is a block diagram illustrating the electrical circuit configuration of a pulse period calculation device according to this embodiment. In this figure, components that are the same as or correspond to those in FIG. 1 are denoted by the same symbols and description thereof will be omitted.

An electrocardiographic sensor 2 and a pulse wave sensor 4 are connected to a pulse period calculation device 3. The pulse wave sensor 4, for example, is attached to a living body such as a human or an animal at a predetermined position and reflected light out of infrared light emitted from a light-emitting diode (LED) is detected by a photodetector, whereby the change in blood flow within a blood vessel with time which changes with the beating of the heart of the living body is detected and output to the pulse period calculation device 3 as a pulse signal, which is a biological signal.

The pulse period calculation device 3 includes an amplifier circuit 20 that amplifies a pulse wave signal output from the pulse wave sensor 4, a filter circuit 21 that removes noise components from the pulse wave signal amplified by the amplifier circuit 20, and an AD converter 22 that converts the pulse wave signal from which noise components have been removed from an analog signal to a digital signal. A signal processing unit 13 converts the pulse wave signal output from the AD converter 22 into an acceleration pulse wave signal by subjecting the pulse wave signal to differentiation two times.

Figure 8:
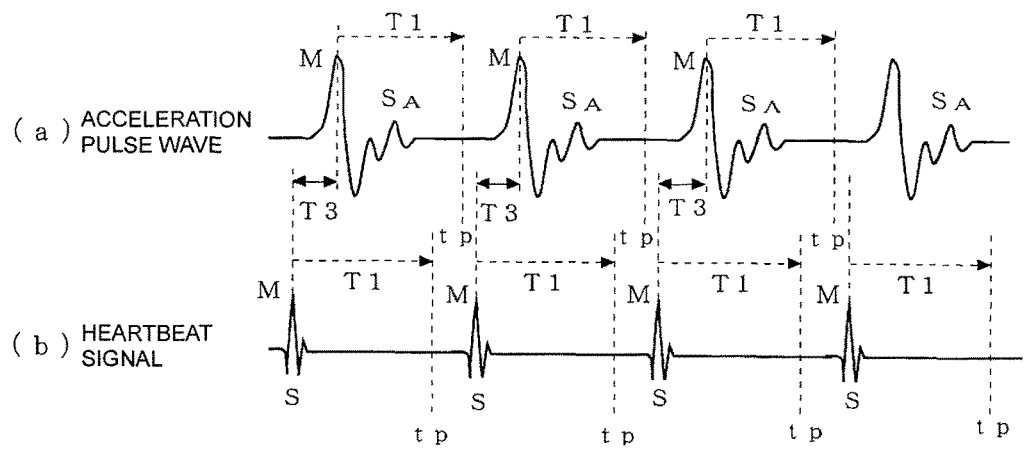
FIG. 8 illustrates a series of acceleration pulse wave signals and a series of heartbeat signals for explaining a pulse wave propagation time period calculated by a signal processing unit of the pulse period calculation device according to the second embodiment.

A pulse wave propagation time period calculation program that simultaneously detects a peak value P of a heartbeat signal and a peak value P of an acceleration pulse wave signal and then calculates a pulse wave propagation time period from a time difference between these values is stored in a ROM of the signal processing unit 13. The pulse wave propagation time period is calculated as a time difference T3 between a peak value P of an acceleration pulse wave signal $S_A$ in a series of acceleration pulse wave signals illustrated in FIG. 8(a) and a peak value P of a heartbeat signal S in a series of heartbeat signals illustrated in FIG. 8(b). Here, the CPU of the signal processing unit 13 functions as maximum value detecting means, peak value determining means, calculating means and fixed time period changing means by utilizing a pulse wave propagation time period calculation program stored in the ROM.

The maximum value detecting means is formed of heartbeat maximum value detecting means that detects a maximum value M of a heartbeat signal S output from the electrocardiographic sensor 2 and obtained at a predetermined time interval and pulse wave maximum value detecting means that detects a maximum value M of an acceleration pulse wave signal $S_A$ acquired by subjecting a pulse wave signal output from the pulse wave sensor 4 obtained at a predetermined time interval to differentiation two times. The peak value determining means is formed of heartbeat peak value determining means that, in the case where a maximum value M that is larger than the maximum value M of the heartbeat signal S detected by the heartbeat maximum value detecting means is not detected by the heartbeat maximum value detecting means within a fixed time period T1 used for heartbeat peak value determination, determines that the maximum value M of the heartbeat signal S detected by the heartbeat maximum value detecting means is a heartbeat peak value P at a peak determination point tp, and pulse wave peak value determining means that, in the case where a maximum value M that is larger than the maximum value M of the acceleration pulse wave signal $S_A$ detected by the pulse wave maximum value detecting means is not detected by the pulse wave maximum value detecting means within a fixed time period T1 used in acceleration pulse wave peak value determination, determines that the maximum value M of the acceleration pulse wave signal $S_A$ detected by the pulse wave maximum value detecting means is a acceleration pulse wave peak value P at a peak determination point tp.

The calculating means calculates the time difference T3 between the heartbeat peak value P determined by the heartbeat peak value determining means and the acceleration pulse wave peak value P determined by the pulse wave peak value determining means as the pulse wave propagation time period. The calculated pulse wave propagation time period is displayed on a display unit 14. The fixed time period changing means is formed of fixed time period changing means, which is for heartbeat peak value determination, that, in accordance with a time interval T2 between successive heartbeat peak values P determined by the heartbeat peak value determining means, successively changes a fixed time period T1 for heartbeat peak value determination to a corresponding one of a plurality of time periods predetermined in accordance with the time interval T2 between heartbeat peak values P, and fixed time period changing means, which is for pulse wave peak value determination, that, in accordance with a time interval T2 between successive acceleration pulse wave peak values P determined by the pulse wave peak value determining means, successively changes a fixed time period T1 for acceleration pulse wave peak value determination to a corresponding one of a plurality of time periods predetermined in accordance with the time interval T2 between the acceleration pulse wave peak values P.

With the pulse period calculation device 3 according to this embodiment, in the case where a maximum value M that is larger than the maximum value M of the heartbeat signal S detected by the heartbeat maximum value detecting means is not detected by the heartbeat maximum value detecting means within the fixed time period T1 for heartbeat peak value determination, the maximum value M of the heartbeat signal S detected by the heartbeat maximum value detecting means is determined to be a heartbeat peak value P by the heartbeat peak value determining means. In addition, in the case where a maximum value M that is larger than the maximum value M of the acceleration pulse wave signal $S_A$ detected by the pulse wave maximum value detecting means is not detected by the pulse wave maximum value detecting means within the fixed time period T1 for acceleration pulse wave peak value determination, the maximum value M of the acceleration pulse wave signal $S_A$ detected by the pulse wave maximum value detecting means is determined to be an acceleration pulse wave peak value P by the pulse wave peak value determining means. Then, the time difference T3 between the heartbeat peak value P determined by the heartbeat peak value determining means and the acceleration pulse wave peak value P determined by the pulse wave peak value determining means is calculated as the pulse wave propagation time period by the calculating means. Accordingly, the time taken for a pulse wave to propagate in an artery due to a pulse is known from the calculated pulse wave propagation time period and therefore the age of a blood vessel can be estimated and the blood pressure can be calculated.

In addition, a pulse rate calculation program, which calculates a pulse rate from the acceleration pulse wave signal SA, which is obtained by subjecting a pulse wave signal acquired at a predetermined interval from the pulse wave sensor 4 to differentiation two times, is provided in the ROM of the signal processing unit 13 of the pulse period calculation device 3 in addition to the heart rate calculation program described in the first embodiment, whereby, together with the pulse wave propagation time period, the heart rate and the pulse rate can be simultaneously calculated and displayed on the display unit 14. In this configuration, by providing the acceleration pulse wave signal $S_A$ to the means that realizes the function of the heart rate calculation program, means that realizes the function of the pulse rate calculation program can be formed and therefore the use of design resources can be reduced.

Next, a third embodiment will be described in which a pulse period calculation device according to the present invention is used to calculate a heart rate.

Figure 9:
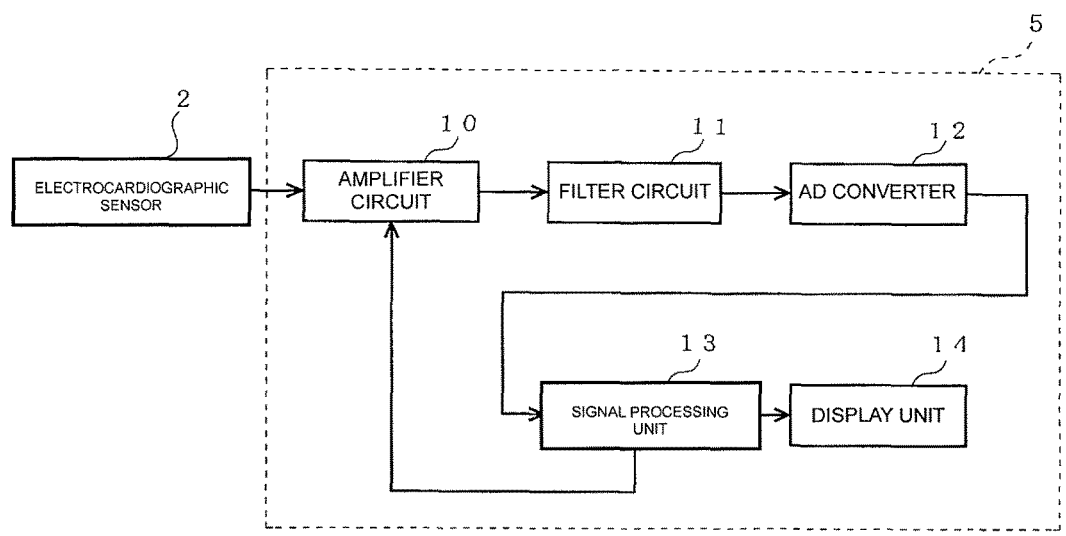
FIG. 9 is a block diagram illustrating the electrical circuit configuration of a pulse period calculation device according to a third embodiment of the present invention.

FIG. 9 is a block diagram illustrating the electrical circuit configuration of a pulse period calculation device according to this embodiment. In this figure, components that are the same as or correspond to those in FIG. 1 are denoted by the same symbols and description thereof will be omitted.

The hardware configuration of a pulse period calculation device 5 according to this embodiment is the same as that of the pulse period calculation device 1 according to the first embodiment except that the signal processing unit 13 and the amplifier circuit 10 are connected to each other, thereby forming a feedback path from the signal processing unit 13 to the amplifier circuit 10.

Also in the pulse period calculation device 5 according to this embodiment, a heartbeat signal output from the electrocardiographic sensor 2 to the pulse period calculation device 5 is amplified by the amplifier circuit 10, but the amplification ratio is determined by a control signal fed back from the signal processing unit 13. The heartbeat signal, which has been amplified at an amplification ratio in accordance with the control signal, is supplied to the maximum value detecting means formed of a CPU inside the signal processing unit 13 via the filter circuit 11 and the AD converter 12. The amplifier circuit 10 is formed of amplifying means that amplifies the heartbeat signal at an amplification ratio in accordance with the control signal and outputs the amplified signal to the maximum value detecting means.

The CPU inside the signal processing unit 13 of this embodiment, as well as functioning as the above-described maximum value detecting means, peak value determining means, calculating means and fixed time period changing means, also functions as reference value detecting means by a heart rate calculation program, which will be described below, stored in the ROM.

As a reference value, the reference value detecting means detects, at a predetermined timing, the magnitude of a heartbeat signal amplified by the amplifier circuit 10. This predetermined timing, in this embodiment, is set to be the timing at which an ST segment of the heartbeat signal, which is illustrated in FIG. 2 and formed of a P wave, a Q wave, an R wave, an S wave, a T wave and a U wave, appears. Here, the term "ST segment" refers to a flat portion between the S wave and the T wave and corresponds to a base line G (refer to FIG. 3), which serves as a reference for the amplitude of the heartbeat signal, and the reference value is detected as a base line value B. In this embodiment, a timing 0.1 [s] after an appearance timing of the R wave detected as a peak value P is taken to be the timing at which the ST segment appears.

In addition, the calculating means of this embodiment calculates the magnitude of a peak value P determined by the peak value determining means from the difference (P−B) between the peak value P determined by the peak value determining means and the base line value B detected by the reference value detecting means and outputs a control signal based on the calculated magnitude of the peak value P to the amplifier circuit 10. For example, in a series of heartbeat signals illustrated in FIG. 10, the calculating means calculates the magnitudes H of the peak values P from the differences (P−B) between the peak values P of the R waves at times t8 and t9 and the base line values B of the ST segments detected at the base line determination points tg, which are at time points 0.1 [s] after the times t8 and t9 at which the peak values P were detected. Then, a control signal based on the magnitudes H of the calculated peak values P is output to the amplifier circuit 10. In this figure, parts that are the same as or correspond to those in FIG. 2 and FIG. 4 will be denoted by the same symbols and description thereof will be omitted.

In addition, in the case where the magnitudes H of peak values P are calculated from the differences (P−B) between a plurality of peak values P successively determined by the peak value determining means and a plurality of base line values B, which are successively detected by the reference value detecting means and correspond to the peak values P, and the magnitudes H of the calculated peak values P successively lie within a predetermined range, the calculating means changes the control signal output to the amplifier circuit 10.

Figure 10:
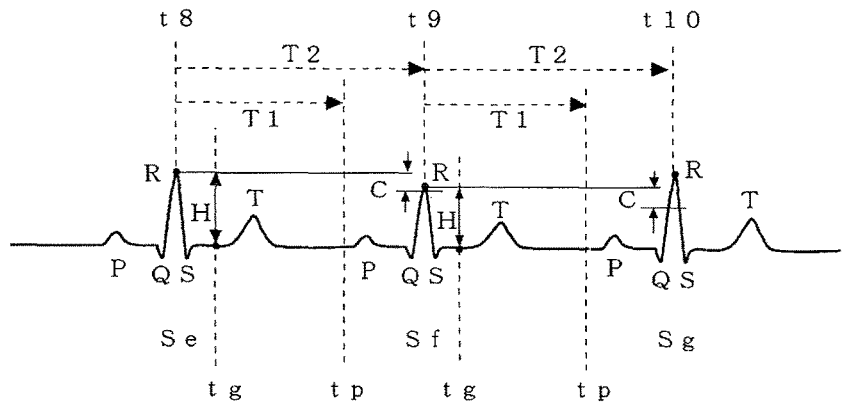
FIG. 10 illustrates a series of heartbeat signals for explaining the magnitude of a peak value calculated from a difference between a peak value and a reference value by a signal processing unit of the pulse period calculation device according to the third embodiment.

For example, in a case in which, in the series of heartbeat signals illustrated in FIG. 11(a), a magnitude H1 of a peak value P of a heartbeat signal Sh is less than a predetermined second threshold Y, but magnitudes H2, H3, H4 and H5 of the peak values of the four subsequent heartbeat signals Si, Sj, Sk and Sl are equal to or larger than the second threshold Y (H≥Y), the level of a determination signal, which is a control signal output to the amplifier circuit 10, is changed. In this figure, parts that are the same as or correspond to those in FIG. 10, are denoted by the same symbols and description thereof is omitted. In this case, at a time t11 in this figure, a control signal output to the amplifier circuit 10 is changed from a High determination signal, which is for a high level, to a Low determination signal, which is for a low level. The amplifier circuit 10, to which the Low determination signal is fed back, amplifies the heartbeat signal S output from the electrocardiographic sensor 2 with a small amplification ratio among two amplification ratios of a large amplification ratio and a small amplification ratio, which were prepared in advance. Therefore, in the signal processing unit 13, thereafter, a heartbeat signal Sm in which the magnitude H of the peak value P has become smaller to H6 is detected.

In addition, in a case in which the magnitudes H7, H8, H9 and H10 of the peak values of four subsequent successive heartbeat signals Sn, So, Sp and Sq are equal to or smaller than a first threshold X (H≤X), a control signal output to the amplifier circuit 10 is changed from a Low determination signal to a High determination signal at a time t12 as illustrated in the figure. The amplifier circuit 10, to which the High determination signal is fed back, amplifies the heartbeat signal S output from the electrocardiographic sensor 2 with the large amplification ratio among the two amplification ratios of the large amplification ratio and the small amplification ratio, which were prepared in advance. Therefore, in the signal processing unit 13, thereafter, a heartbeat signal Sr in which the magnitude H of the peak value P has become larger to H11 is detected.

Next, heart rate calculation processing performed by the CPU in accordance with the heart rate calculation program stored in the ROM in the signal processing unit 13 of the pulse period calculation device 5 according to this embodiment will be described while referring to the flowchart of FIG. 12. In this figure, steps that are the same as or correspond to those of the flowchart of FIG. 5 are denoted by the same step symbols and description thereof will be omitted.

In the case where the maximum value M of the heartbeat signal amplified by the amplifier circuit 10 and obtained in S1 is not greater than the current maximum value M stored in the RAM and the determination result of S11 is No, the CPU, in S13, counts up a count value of the maximum value update counter and a count value of the peak interval counter and timing progresses. Next, the CPU, in S21, determines whether a time period timed by the maximum value update counter has reached a base line determination point tg at which the ST segment appears, which is a time point 0.1 [s] after a timing at which the latest peak value P stored in the RAM appeared. In the case where 0.1 [s] has elapsed and the determination result of S21 is Yes, the CPU, in S22, stores in the RAM as the base line value B an input value from the electrocardiographic sensor 2 at the time point at which it has been timed by the maximum value update counter that 0.1 [s] has elapsed, returns to the processing of S1 and repeats performance of the above-described processing operations.

On the other hand, in the case where 0.1 [s] has not elapsed and the determination result of S21 is No, the CPU, in S14, as has been described above, determines whether the time period timed by the maximum value update counter has exceeded the fixed time period T1. In the case where the time period timed by the maximum value update counter is more than the fixed time period T1 and the determination result of S14 is Yes, the CPU, in S23, calculates the difference between the latest peak value P stored in the RAM and the base line value B stored in the RAM in S22, that is, calculates the magnitude H of the peak value P.

Next, the CPU, in S24, determines whether or not the difference between the calculated peak value P and base line value B is less than or equal to the first threshold X, that is, whether the magnitude H of the latest peak value P stored in the RAM is small. In the case where the difference between the peak value P and the base line value B is equal to or less than the first threshold X, that is, the magnitude H of the latest peak value P is small and the determination result of S24 is Yes, the CPU, in S25, determines whether or not it has been successively detected four times that a difference between a peak value P and a base line value B is equal to or less than the first threshold X as in the case of the heartbeat signals Sn, So, Sp and Sq illustrated in FIG. 11. In the case where it has been detected that the difference has been successively smaller than the first threshold X four times and the determination result of S25 is Yes, the CPU, in S26, changes the determination signal fed back to the amplifier circuit 10 to for example High from Low at time t12. Consequently, the amplification ratio of the amplifier circuit 10 becomes the large amplification ratio and the heartbeat signal output from the electrocardiographic sensor 2 becomes an appropriate signal in which the magnitude H11 of the peak value P is large as in for example the heartbeat signal Sr.

On the other hand, in the case where the difference between the peak value P and the base line value B is not equal to or less than the first threshold X and the determination result of S24 is No, the CPU, in S27, determines whether the difference between the peak value P and the base line value B calculated in S23 is equal to or more than a second threshold Y, that is, whether the magnitude H of the latest peak value P stored in the RAM is large. In the case where the difference between the peak value P and the base line value B is equal to or more than the second threshold Y, that is, the magnitude H of the latest peak value P is large and the determination result of S27 is Yes, the CPU, in S28, determines whether or not it has been successively detected four times that a difference between a peak value P and a base line value B is equal to or larger than the second threshold Y as in the case of the heartbeat signals Si, Sj, Sk and Sl illustrated in FIG. 11. In the case where it has been detected that the difference has been successively larger than the second threshold Y four times and the determination result of S28 is Yes, the CPU, in S29, changes the determination signal fed back to the amplifier circuit 10 to for example Low from High at time, t11. Consequently, the amplification ratio of the amplifier circuit 10 becomes the small amplification ratio and the heartbeat signal output from the electrocardiographic sensor 2 becomes an appropriate signal in which the magnitude H6 of the peak value P is small as in for example the heartbeat signal Sm.

In the case where such a difference is not successively detected four times and the determination result of S25 or S28 is No, or in the case in which the determination signal level is changed and the processing of S26 or S29 finishes, next, the CPU, in S15, as has been described above, determines that the maximum value M of the heartbeat signal obtained in S1 is a peak value P, sets the maximum value M as the latest peak value P in the RAM, obtains the number of peak values P per minute to calculate the heart rate, and resets the maximum value update counter and the maximum value M determined to be the peak value P this time.

Figure 12:
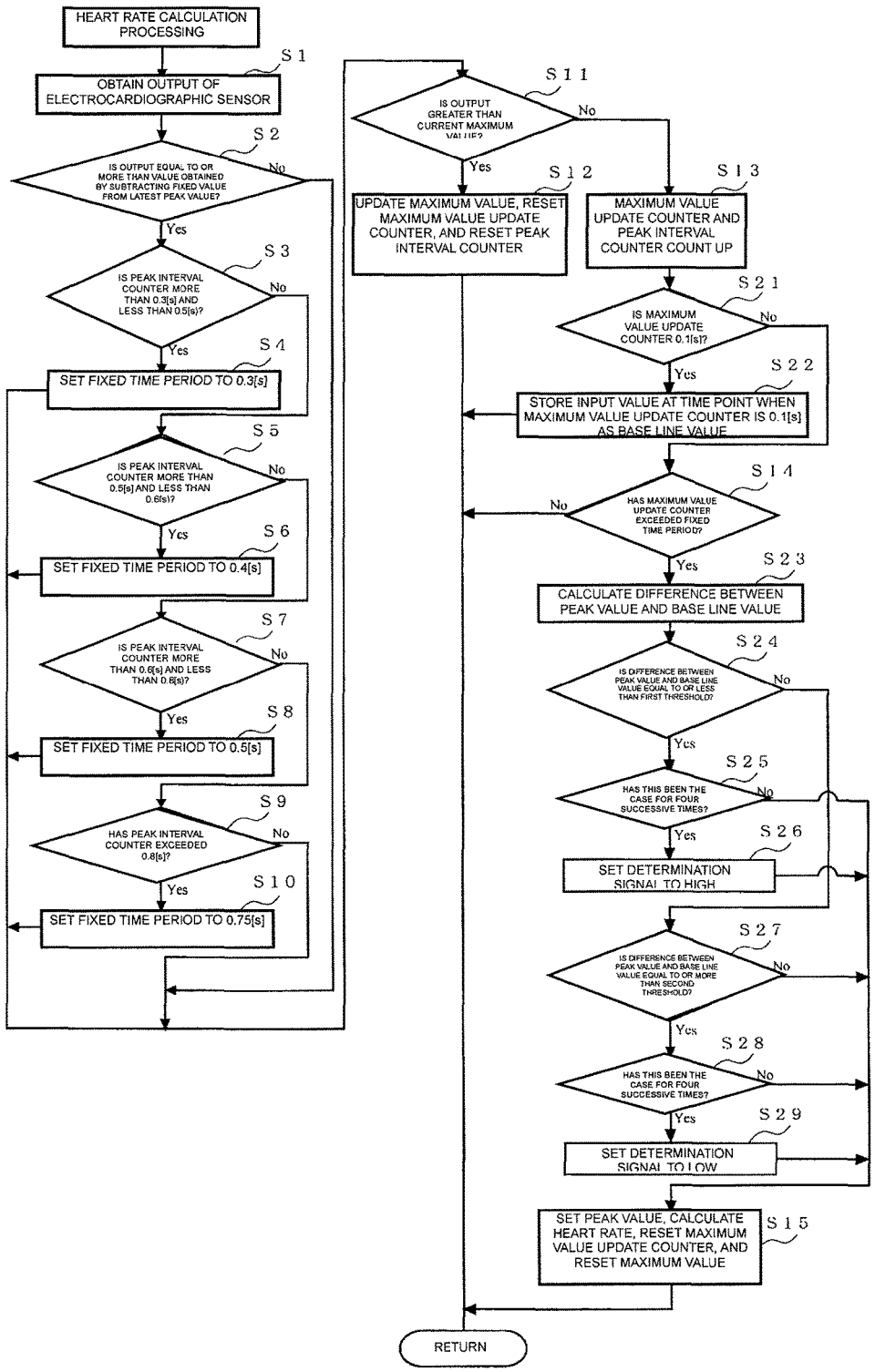
FIG. 12 is a flowchart illustrating heart rate calculation processing performed by the signal processing unit of the pulse period calculation device according to the third embodiment.

With the pulse period calculation device 5 according to this embodiment, the magnitude H of a peak value P is calculated by the calculating means in S23 of FIG. 12 from the difference between the peak value P determined by the peak value determining means and a base line value B detected by the reference value detecting means. Then, a control signal based on the magnitude H of the calculated peak value P is made to be a High or Low determination signal in S26 or S29 and output to the amplifier circuit 10 and the amplification ratio of the amplifier circuit 10 is changed.

That is, in the case where the calculated magnitude H of the peak value P is larger than the second threshold Y, the control signal is changed to a Low determination signal that makes the amplification ratio of the amplifier circuit 10 small, whereas in the case where the calculated magnitude H of the peak value P is smaller than the first threshold X, the control signal is changed to a High determination signal that makes the amplification ratio of the amplifier circuit 10 large. Consequently, the magnitude of the heartbeat signal obtained though amplification performed by the amplifier circuit 10 is appropriately controlled to be a magnitude that is suitable for maximum value detection of a heartbeat signal by the maximum value detecting means in S11 and S12 and that is suitable for determination of the peak value P by the peak value determining means in S14 and S15. As a result, erroneous detection of the maximum value of a heartbeat signal by the maximum value detecting means and erroneous determination of a peak value P by the peak value determining means is avoided and the accuracy with which the peak value P is detected is improved.

In addition, with the pulse period calculation device 5 according to this embodiment, a reference value detected by the reference value detecting means is the value of an ST segment of a heartbeat signal, that is, a base line value B, which serves as a reference for the amplitude of a heartbeat signal. Consequently, the magnitude H of a peak value P calculated by the calculating means is a magnitude with respect to the base line G (refer to FIG. 3) and is easy to evaluate.

Figure 11:
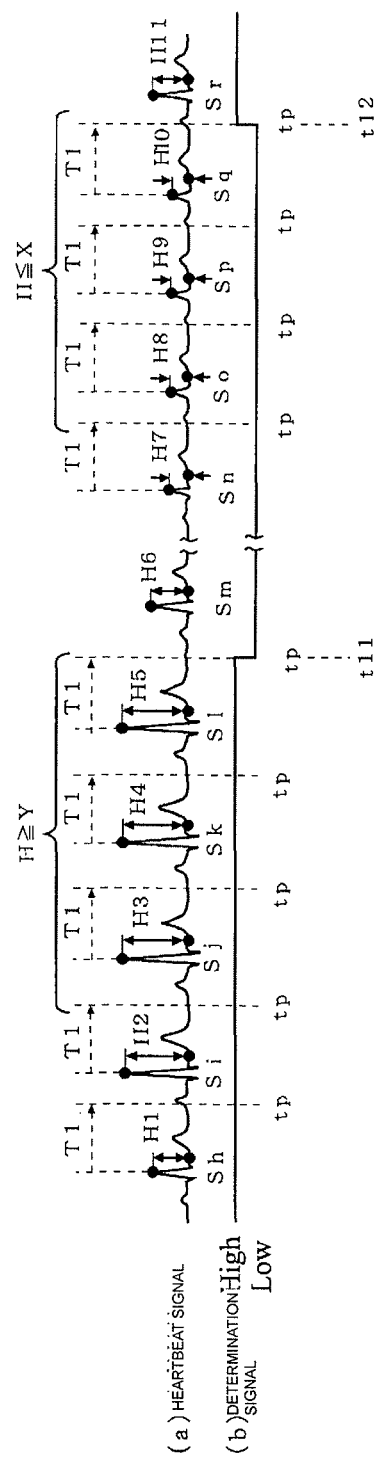
FIG. 11 illustrates a series of heartbeat signals and a determination signal, which serves as a control signal, for explaining the magnitudes of peak values calculated from differences between a plurality of successive peak values and a plurality of successive reference values by the signal processing unit of the pulse period calculation device according to the third embodiment.

In addition, with the pulse period calculation device 5 according to this embodiment, in the case where the differences between a plurality of peak values P and a plurality of base line values B calculated by the calculating means are successively within a predetermined range, the control signal fed back to the amplifier circuit 10 is changed and the amplification ratio of the amplifier circuit 10 is changed. For example, in the case where the differences between the peak values P and the base line values B of the heartbeat signals Si, Sj, Sk and Sl illustrated in FIG. 11 are successively within a predetermined range of being equal to or greater than the second threshold Y (H≥Y) and the magnitudes H of the peak values P are successively large, the control signal output to the amplifier circuit 10 is changed to a Low determination signal from a High determination signal at the time t11 and the amplification ratio of the amplifier circuit 10 is changed to a small amplification ratio. In addition, in the case where the differences between the peak values P and the base line values B of the heartbeat signals Sn, So, Sp and Sq illustrated in FIG. 11 are successively within a predetermined range of being equal or less than the first threshold X (H≤X) and the magnitudes H of the peak values P are successively small, the control signal output to the amplifier circuit 10 is changed to a High determination signal from a Low determination signal at the time t12 and the amplification ratio of the amplifier circuit 10 is changed to a large amplification ratio. Consequently, in the case where the magnitudes H of peak values P successively and stably remain within a predetermined range, the amplification ratio of the amplifier circuit 10 is changed and therefore erroneous changing of the amplification ratio of the amplifier circuit 10 due to erroneous determination of the magnitude H of a peak value P is avoided.

In the above-described embodiment, a configuration has been described in which in the case where the magnitudes H of the peak values P of four successive heartbeat signals are equal to or less than the first threshold X or equal to or more than the second threshold Y, the level of a determination signal is changed, but the present invention is not limited to, this configuration. For example, a configuration may be adopted in which the level of a determination signal is changed in the case where the magnitudes H of the peak values P of two, three or five or more successive heartbeat signals are equal to or less than the first threshold X or equal to or more than the second threshold Y. In addition, a configuration may be adopted in which the level of a determination signal is changed in the case where the magnitude H of the peak value P of a single heartbeat signal is equal to or less than the first threshold X or equal to or more than the second threshold Y.

In addition, in the above-described embodiment, a case was described in which two thresholds, that is, first and second thresholds, used for determining the magnitude H of a peak value P are employed, but the present invention is not limited to this. For example, a configuration may be adopted in which the amplification ratio of the amplifier circuit 10 is set to any of three or more values by adopting three or more thresholds, subjecting the magnitude H of a peak value P to finer determination and increasing the number of types of determination signal.

In addition, in the above-described embodiment, the base line determination point tg at which the ST segment appears was a time 0.1 [s] after a timing at which the peak value P appeared and the magnitude of the heartbeat signal at that one time point was the baseline value B. However, a configuration may be adopted in which a plurality of time points including and before and after a time point 0.1 [s] after the timing at which the peak value P appears serve as a plurality of base line determination points tg and in which an average value of the magnitudes of the heartbeat signals at these plurality of base line determination points tg serve as the base line value B. With this configuration, the accuracy with which the base line value B is detected is improved and the magnitude H of a peak value P is calculated with greater accuracy.

In addition, in the above-described embodiment, a case was described in which a reference value detected by the reference value detecting means was taken to be a base line value B at which an ST segment appears, but the present invention is not limited to this. For example, a configuration may be adopted in which for example the magnitude of a heartbeat signal at a time when the peak value of a T wave appears after an S wave, or the magnitude of a heartbeat signal in a flat component that appears between a P wave and a Q wave serves as a reference value and the difference between this reference value and a peak value P is detected as the magnitude H of the peak value P.

In addition, in the above-described embodiment, a case was described in which an amplification ratio of the amplifier circuit 10 is subjected to feedback control in a device configuration in which a biological signal is a heartbeat signal detected by the electrocardiographic sensor 2 and the rhythmic period of a pulse is calculated as a heart rate, but the present invention is not limited to this. For example, the amplification ratio of the amplifier circuit may be subjected to feedback control in a device configuration in which the biological signal is a pulse wave signal detected by a pulse wave sensor and the rhythmic period of the pulse is calculated as a pulse rate. In addition, as in the pulse period calculation device 3 illustrated in FIG. 7, each of the amplification ratios of the amplifier circuit 10 and the amplifier circuit 20 may be subjected to feedback control in a device configuration in which biological signals are a heartbeat signal detected by the electrocardiographic sensor 2 and a pulse wave signal detected by the pulse wave sensor 4 and the rhythmic period of the pulse is calculated as a heart rate and a pulse rate and the pulse wave propagation time period is calculated.

In addition, the signal processing units 13 of the pulse period calculation devices 1, 3, and 5 according to the first, second and third embodiments can be formed of for example an application specific integrated circuit (ASIC), a field programmable gate array (FPGA) or a digital signal processor (DSP).

A bio-sensor can be formed that is equipped with the pulse period calculation device 1 according to the first embodiment, which calculates a heart rate and a pulse rate, and the electrocardiographic sensor 2 and the pulse wave sensor 4. With this configuration, a bio-sensor is provided that exhibits each of the effects of the pulse period calculation device 1 according to the first embodiment. Similarly, a bio-sensor can be formed that is equipped with the pulse period calculation device 3 according to the second embodiment, which calculates the pulse wave propagation time period, and the electrocardiographic sensor 2 and the pulse wave sensor 4. With this configuration, a bio-sensor is provided that exhibits each of the effects of the pulse period calculation device 3 according to the second embodiment. Similarly, a bio-sensor can be formed that is equipped with the pulse period calculation device 5 according to the third embodiment, in which the amplification ratio of the amplifier circuit 10, which amplifies a heartbeat signal, and the amplification ratio of the amplifier circuit 20, which amplifies a pulse wave signal, are subjected to feedback control, and is also equipped with the electrocardiographic sensor 2 and the pulse wave sensor 4. With this configuration, a bio-sensor is provided that exhibits each of the effects of the pulse period calculation device 5 according to the third embodiment.

REFERENCE SIGNS LIST 1, 3 . . . pulse period calculation device
2 . . . electrocardiographic sensor
4 . . . pulse wave sensor
10, 20 . . . amplifier circuit
11, 21 . . . filter circuit
12, 22 . . . AD converter
13 . . . signal processing unit
14 . . . display unit
T1 . . . fixed time period
T2 . . . time interval between peak values
T3 . . . time difference (pulse wave propagation time period)
M . . . maximum value
tp . . . peak determination point
tg . . . base line determination point
C . . . fixed value G . . . base line
H . . . magnitude of peak value

The invention claimed is:

1. A pulse period calculation device for calculating a rhythmic pulse period of a living body, the device comprising:
   a maximum value detecting unit configured to determine a maximum value of a biological signal of the living body by detecting a highest value of the biological signal during a predetermined time interval and selecting the highest value of the biological signal as the maximum value;
   a peak value determining unit configured to determine that the determined maximum value is a peak value of the biological signal when the maximum value detecting unit does not detect a new value of the biological signal during a fixed time period following the determined maximum value that is greater than the highest value of the biological signal selected as the determined maximum value;
   a calculating unit configured to calculate the rhythmic pulse period of the living body based on a measured time interval between successive peaks of the determined peak value of the biological signal when the measured time interval between the successive peaks is greater than the fixed time period; and
   a fixed time period changing unit configured to select, as an updated fixed time period, one of a plurality of predetermined time periods based on the measured time interval between the successive peaks of the determined peak value of the biological signal,
   wherein, when the maximum value detecting unit determines that the highest value of the biological signal detected during the updated fixed time period following a current peak value of the biological signal is greater than the determined maximum value, the peak value determining unit updates the peak value of the biological signal to be the highest value of the biological signal detected during the updated fixed time period, and
   wherein the calculating unit is further configured to update the rhythmic pulse period based on a measured time interval between successive peaks of the updated peak value when the measured time interval between the successive peaks of the updated peak value is greater than the updated fixed time period.

2. The pulse period calculation device according to claim 1, wherein the fixed time period changing unit is further configured to successively change the updated fixed time period when the successive peaks of the determined peak value each fall within a predetermined range.

3. The pulse period calculation device according to claim 1, wherein the biological signal is a heartbeat signal of the living body and the rhythmic pulse period is a heart rate of the living body.

4. The pulse period calculation device according to claim 1, wherein the biological signal is a pulse wave signal and the rhythmic pulse period is a pulse rate.

5. The pulse period calculation device according to claim 1,
   wherein the maximum value detecting unit comprises:
      a heartbeat maximum value detecting unit configured to detect a maximum value of a heartbeat signal received at the predetermined time interval, and
      a pulse wave maximum value detecting unit configured to detect a maximum value of an acceleration pulse wave signal obtained by subjecting a pulse wave signal measured at the predetermined time interval to differentiation two times, wherein the peak value determining unit comprises:
      a heartbeat peak value determining unit configured to determine whether the detected maximum value of the heartbeat signal is a heartbeat peak value detected by the heartbeat maximum value detecting unit during the fixed time period, and
      a pulse wave peak value determining unit configured to determine whether the detected maximum value of the acceleration pulse wave signal is an acceleration pulse wave peak value,
   wherein the calculating unit is further configured to calculate a pulse wave propagation time period from a time difference between the heartbeat peak value and the acceleration pulse wave peak value, and
   wherein the fixed time period changing unit is further configured to successively change the fixed time period used for heartbeat peak value determination to one of a plurality of predetermined time periods that corresponds to the time interval between the heartbeat peak values, and to successively change the fixed time period for acceleration pulse wave peak value determination to one of a plurality of predetermined time periods that corresponds to the time interval between the acceleration pulse wave peak values.

6. The pulse period calculation device according to claim 1, further comprising:
   an amplifying unit configured to amplify the biological signal at an amplification ratio according to a control signal and to output the amplified signal to the maximum value detecting unit; and
   a reference value detecting unit configured to detect a magnitude of the amplified biological signal at a predetermined timing as a reference value,
   wherein the calculating unit is further configured to calculate a magnitude of the determined peak value of the biological signal based on a difference between the peak value of the biological signal and the reference value and to output to the amplifying unit the control signal, which is based on the magnitude of the determined peak value of the biological signal.

7. The pulse period calculation device according to claim 6, wherein the biological signal is composed of a P wave, a Q wave, an R wave, an S wave, a T wave and a U wave, and the predetermined timing is based on an ST segment of the biological signal.

8. The pulse period calculation device according to claim 6, wherein the calculating unit is further configured to calculate respective magnitudes of peak values based on differences between a plurality of successive peak values of the biological signal and a plurality of reference values that correspond to the plurality of successive peak values, respectively, and to change the control signal when the calculated respective magnitudes of the peak values are successively within a predetermined range.

9. The pulse period calculation device according to claim 1, wherein the peak value determining unit is further configured to determine that the determined maximum value is the peak value of the biological signal when the determined maximum value is larger than or equal to a previous peak value of the rhythmic pulse stored in memory minus a fixed value and when the maximum value detecting unit does not detect a new value of the biological signal during the fixed time period following the determined maximum value that is greater than the highest value of the biological signal.

10. The pulse period calculation device according to claim 1, wherein the peak value determining unit is further configured to determine that the determined maximum value is the peak value of the biological signal when the determined maximum value is determined to be a normal peak value and when the maximum value detecting unit does not detect a new value of the biological signal during the fixed time period following the determined maximum value that is greater than the highest value of the biological signal.

11. A bio-sensor comprising the pulse period calculation device according to claim 1.

12. A pulse period calculation device for calculating a rhythmic pulse period of a living body, the pulse period calculation device comprising a processor configured to:
   determine a maximum value of a biological signal of the living body by detecting a highest value of the biological signal during a predetermined time interval and selecting the highest value of the biological signal as the maximum value;
   determine that the determined maximum value is a peak value of the biological signal when a new value of the biological signal is not detected during a fixed time period following the determined maximum value that is greater than the highest value of the biological signal selected as the determined maximum value;
   calculate the rhythmic pulse period of the living body based on a measured time interval between successive peaks of the determined peak value of the biological signal when the measured time interval between the successive peaks is greater than the fixed time period;
   select, as an updated fixed time period, one of a plurality of predetermined time periods as a changed fixed time period based on the measured time interval between the successive peaks of the determined peak value of the biological signal;
   update the peak value of the biological signal to be the highest value of the biological signal detected during the updated fixed time period when the highest value of the biological signal detected during the updated fixed time period following a current peak value of the biological signal is greater than the determined maximum value detected at the fixed time period; and
   update the rhythmic pulse period based on a measured time interval between successive peaks of the updated peak value when the measured time interval between the successive peaks of the updated peak value is greater than the updated fixed time period.

13. The pulse period calculation device according to claim 12, wherein the processor is further configured to successively change the updated fixed time period when the successive peaks of the determined peak value each fall within a predetermined range.

14. The pulse period calculation device according to claim 12, further comprising:
   an amplifying unit configured to amplify the biological signal at an amplification ratio according to a control signal and to output the amplified signal to the processor,
   wherein the processor is further configured to detect a magnitude of the amplified biological signal at a predetermined timing as a reference value, to calculate a magnitude of the determined peak value of the biological signal based on a difference between the peak value of the biological signal and the reference value, and to output to the amplifying unit the control signal, which is based on the magnitude of the determined peak value of the biological signal.

15. The pulse period calculation device according to claim 14, wherein the processor is further configured to calculate respective magnitudes of peak values based on differences between a plurality of successive peak values of the biological signal and a plurality of reference values that correspond to the plurality of successive peak values, respectively, and to change the control signal when the calculated respective magnitudes of the peak values are successively within a predetermined range.

16. A pulse period calculation method for calculating a rhythmic pulse period of a living body, the method comprising:
   determining a first maximum value of a biological signal of the living body by detecting a highest value of the biological signal during a predetermined time interval and selecting the highest value of the biological signal as the maximum value;
   determining that the determined maximum value is a peak value of the biological signal when a new value of the biological signal is not detected during a fixed time period following the determined maximum value that is greater than the highest value of the biological signal selected as the determined maximum value;
   calculating the rhythmic pulse period of the living body based on a measured time interval between successive peaks of the determined peak value of the biological signal when the measured time interval between the successive peaks is greater than the fixed time period; and
   selecting, as an updated fixed time period, one of a plurality of predetermined time periods based on the measured time interval between the successive peaks of the determined peak value of the biological signal;
   updating the peak value of the biological signal to be the highest value of the biological signal detected during the updated fixed time period when the highest value of the biological signal detected during the updated fixed time period following a current peak value of the biological signal is greater than the determined maximum value detected at the fixed time period; and
   updating the rhythmic pulse period based on a measured time interval between successive peaks of the updated peak value when the measured time interval between the successive peaks of the updated peak value is greater than the updated fixed time period.

17. The pulse period calculation method according to claim 16, further comprising:
   successively changing the updated fixed time period when the successive peaks of the determined peak value each fall within a predetermined range.

18. The pulse period calculation method according to claim 16, further comprising:
   amplifying the biological signal at an amplification ratio according to a control signal;
   detecting a magnitude of the amplified biological signal at a predetermined timing as a reference value;
   calculating a magnitude of the determined peak value of the biological signal based on a difference between the peak value of the biological signal and the reference value; and
   adjusting the control signal based on the magnitude of the determined peak value of the biological signal.

19. The pulse period calculation method according to claim 18, further comprising:
   calculating respective magnitudes of peak values based on differences between a plurality of successive peak values of the biological signal and a plurality of reference values that correspond to the plurality of successive peak values, respectively; and changing the control signal when the calculated respective magnitudes of the peak values are successively within a predetermined range.

\* \* \* \* \*